United States Patent [19]

Glaser

[11] Patent Number: 4,996,159

[45] Date of Patent: Feb. 26, 1991

[54] NEOVASCULARIZATION INHIBITORS AND METHODS FOR THEIR PRODUCTION AND USE

[75] Inventor: Bert M. Glaser, Owings Mills, Md.

[73] Assignee: The Johns Hopkins University, Baltimore, Md.

[21] Appl. No.: 471,024

[22] Filed: Jan. 26, 1990

Related U.S. Application Data

[63] Continuation of Ser. No. 706,259, Feb. 26, 1985, abandoned.

[51] Int. Cl.$^5$ ............... C12P 21/00; C07K 3/00; C07K 15/06; A61K 37/02
[52] U.S. Cl. ............... 435/70.3; 435/70.1; 530/350; 530/849; 514/21
[58] Field of Search ............... 435/70.1, 70.3, 240.2, 435/240.23; 424/571; 514/21, 866, 912; 530/350, 412, 413, 414, 417, 849

[56] References Cited

U.S. PATENT DOCUMENTS

| Re. 30,239 | 3/1980 | Kuettner et al. | 424/95 |
|---|---|---|---|
| 4,042,457 | 8/1977 | Kuetner et al. | 424/95 |
| 4,182,753 | 1/1980 | Saltarelli | 264/54 |
| 4,356,261 | 10/1982 | Kuetner | 435/68 |
| 4,534,967 | 8/1985 | Jacobson et al. | 424/95 |

OTHER PUBLICATIONS

Graham et al., "Differences in Proteins Secreted by Human Fibroblasts and Muscle Cells in Culture", Experimental Cell Research, vol. 154, pp. 321-325, 1984.
Oka et al., "A serum free defined medium for retinal pigment epithelial cells", Experimental Cell Research, vol. 154, pp. 537-547, 1984.
Sly et al., "Isolation of Fibroblasts from Patients", Methods in Enzymology, vol. LVIII, pp. 444-450, 1979.
Griffiths, "Cell Products: An Overview", in *Animal Cell Biotechnology*, vol. 2, pp. 3-12, 1985, Academic Press Inc., London, Eng.
Li et al., "Extracellular Matrix Production by Cat Retinal Pigment Epithelium in vitro: Characterization of Type IV Collagen Synthesis", Exp. Eye Res., vol. 38, pp. 29-304, 1984.
Glaser et al., Arch Ophthalmol (1985), vol. 103, pp. 1870-1875.
Cunha-Vaz, "The Blood-Retinal Barriers", Documenta Ophthalmologica, vol. 41 (2), pp. 287-327, 1976.
Kuwabara, Toichiro, "The Eye", *Histology: Cell and Tissue Biology*, Weiss, L., Ed., Fifth ed., McGraw-Hill, Inc., New York, 1983, pp. 1155-1164.
Sholley et al., Radiation Response of Corneal Neovascularization, *Investigative Opthalmology and Visual Science*, 1980, Supplement, p. 254.
Zinn and Benjamin-Henkind, Retinal Pigment Epithelium, *Ocular Anatomy, Embryology, and Teratology*, Frederick A. Jakobiec, Editor, Harper & Row, 1982, pp. 533-537.
Dorland's Illustrated Medical Dictionary, Twenty-sixth Ed., p. 1016.
Schweigerer et al., Nature, 325:257-259 (1987).
Kuettner and Pauli, "Vascularity of Cartilage," Cartilage: Structure, Function, and Biochemistry, vol. 1 (Academic Press Inc., 1983), p. 285.
Peyman et al., Intravitreal Surgery: Principles and Practice (Appleton-Century-Crofts, 1986), pp. 2, 5, 8.
Histology: Cell and Tissue Biology, L. Weiss, Editor, 5th Ed., (Elsevier Biomedical, New York, 1983), pp. 397, 402, 1157.
Biomedical Foundations of Ophthamology, Duane & Jaeger, Editors, (Harper & Row, 1986), ch. 21, p. 12.
Adler's Physiology of the Eye: Clinical Application, Moses, Editor, (C. V. Mosby Co., 1981), p. 191.
Biomedical Foundations of Ophthamology, Duane & Jaeger, Editors, vol. 1, chap. 15, p. 3.
Peyman et al., Intravitreal Surgery: Principles and Practice, (Appleton-Century-Crofts, 1986), p. 5.
Campochiaro and Glaser, Arch. Ophthalmol., 103: 1876-1880, (Dec. 1985).
Green, Tr. Am. Ophthl. Soc., 75: 180-254 (1977).
Hogan, Tr. Am. Acad. Ophth. & Otol., 76: 64-80 (1972).
Jacobsen et al., Arch Opthalmol., 102: 1543-1545, 1984.
Williams et al., Am. J. Opthalmol., 97: 366-371, 1984.
Lutty et al., Investigative Opthalmology and Visual Science, 23: 52-56, 1983.
Patz et al., Opthalmology, 85: 626-637, 1978.
Preis et al., Am. J. Opthalmol., 84: 323-328, 1977.
Lee et al., Science, 221: 1185-1187, 1983.
Pauli et al., The Regulation of Invasion by a Cartilage-Derived Anti-Invasion Factor, Liotta and Hart (eds.), *Tumor Invasion and Metastasis* (Martinu Nijhoff Publishers, 1982), pp. 267-290.
Langer et al., Proc. Natl. Acad. Sci., USA, 77: 4331-4335, 1980.
Langer et al., Science, 193: 70-72, 1976.
Eisenstein et al., Am. J. Opthamol., 88: 1005-1012, 1979.
Goren et al., Am. J. Opthamol., 84: 305-309, 1977.
Taylor et al., Nature, 297: 307-312, 1982.
Maugh, Science, 212: 1374-1375, 1981.
Eisenstein et al., Am. J. Pathol., 765-772, 1973.
Sorgente et al., Laboratory Investigation, 32: 217-222, 1975.
Eisenstein et al., Am. J. Pathol., 81: 337-348, 1975.
Folkman et al., Science, 221: 719-725, 1983.
Wolbarsht et al., Opthalmic Surgery, 111: 235-245, 1980.
Stefansson et al., Tr. Am. Ophth. Soc., 79: 307-334, 1981.
Foulds, Trans. Opthal. Soc. N.Z., 32: 82-90, 1980.
Korte et al., Invest. Opthamol. Vis. Sci., 25: 1135-1145, 1984.
Heriot et al., Opthalmology, 91: 1603-1608, 1984.

*Primary Examiner*—Elizabeth C. Weimar
*Assistant Examiner*—Gail Poulos
*Attorney, Agent, or Firm*—Dickstein, Shapiro & Morin

[57] ABSTRACT

Neovascularization inhibitors are disclosed, which are purified polypeptides recovered from cultured cells, including retinal pigment epithelial cells and human fibroblast cells. The polypeptides may be used for the treatment of diseases in which new blood vessel formation plays a role, such as diabetic retinopathy, senile macular degeneration, tumor growth, and rheumatoid arthritis.

13 Claims, No Drawings

NEOVASCULARIZATION INHIBITORS AND METHODS FOR THEIR PRODUCTION AND USE

This application is a continuation of application Ser. No. 706,259 filed Feb. 26, 1985.

BACKGROUND OF THE INVENTION

This invention relates to substances that inhibit neovascularization and to methods for their production and use.

Neovascularization plays a crucial role in the pathogenesis of several important human disorders, including diabetic retinopathy, senile macular degeneration, tumor growth, rheumatoid arthritis, and excessive scarring during wound healing. In diabetic retinopathy, new blood vessels grow from the optic disc and retina, which eventually can cause blindness. Laser treatment has been shown to reduce blindness from this disorder, but the destruction caused by the formation of retinal scars causes dramatic reductions in peripheral vision and night vision. Pharmacologic inhibitors of neovascularization could provide improved treatment modalities for patients with this disease.

In senile macular degeneration, new blood vessels grow through Bruch's membrane to invade the retina. This retinal invasion causes destruction of the photoreceptors and thereby reduces vision. Inhibitors of neovascularization could prevent or limit loss of vision.

The process of tumor growth and invasion is one of the major causes of mortality in the industrialized nations. The inhibition of neovascularization has been shown to induce the regression of tumors. Availability of therapeutic quantities of a potent inhibitor of neovascularization could provide an important adjunct to current cancer therapy.

In rheumatoid arthritis, the articular cartilage of the involved joint is invaded by a vascular pannus. This vascular tissue destroys the normal smooth cartilage surface. Inhibition of neovascularization could lessen the joint destruction that occurs in rheumatoid arthritis.

Excessive scarring during wound healing, such as in the case of keloids, may cause significant disfiguration. Since neovascularization is an important component of wound healing and scar formation, its inhibition may control keloid formation.

The possibility that controlling neovascularization will aid in the treatment of these disorders has prompted an extensive search for inhibitors of new blood vessel formation. Most inhibitors of neovascularization so far identified have been extracted from tissues that are avascular, such as cartilage, vitreous, and lens. For example, Jacobson et al. found a low molecular weight (less than 13,000 daltons) substance or substances that inhibited aortic endotheolial cell proliferation in several isolates that had been derived from human vitreous. The isolates had been physically extracted from the vitreous, centrifuged, and subjected to gel chromatography. Jacobson et al., *Arch. Ophthalmol.*, 102, 1543 (1984). Williams et al. described a substance with a molecular weight of less than 100,000 that inhibited bovine aortic endothelial cell proliferation. The substance was extracted from human and bovine lenses by 1 M quanidine hydrochloride and was passed through a membrane with a molecular weight cut-off of 100,000 daltons. Williams, et al., *Am. J. Ophthalmol.*, 97, 366 (1984). Lutty et al. described an extract from adult bovine vitreous that inhibited neovascularization. The extract was prepared by homogenizing the vitreous, incubating it with sodium ascorbate, dialyzing it (12,000–14,000 molecular weight cut-off), and filter-sterilizing the dialyzate. Lutty et al., *Investigative Ophthalmology and Visual Science*, 23, 52 (1983). Brem et al. found a factor extracted from rabbit vitreous that inhibited the growth of new blood vessels induced by tumors in rabbit corneas. The factor was extracted by centrifuging vitreous and dialyzing the supernatant, using cellulose tubing with a 12,000 molecular weight limit. Brem et al., *Am. J. Ophthalmol.*, 84, 323 (1977).

Unfortunately, these substances presently are not useful for the treatment of diseases involving neovascularization. Only limited quantities of inhibitors can be extracted from the previously mentioned sources, and the inhibitors have been only partially purified and characterized. In fact, the limited quantities and relatively unpurified state of these substances have made it difficult even to evaluate their potential for use in the treatment of disease.

U.S. Pat. No. 4,356,261 to Kuettner discloses a process for producing a neovascularization inhibitor derived from cartilage, which is intended to overcome the problem of the limited supply of such substances. The method involves culturing cartilage producing cells at high density and extracting the inhibitor from the culture. The extraction process is disclosed in U.S. Pat. No. 4,042,457 to Kuettner et al. The process involves the use of an aqueous extraction medium that includes a solute that does not irreversibly denature the proteinaceous material to be extracted, preferably a 1.0–3.0 M aqueous solution of quanidine hydrochloride, separating the extract, recovering substances having a molecular weight below about 50,000, treating such substances to remove salts therefrom, and dehydrating the resultant material. The substance or substances, which has a molecular weight of 50,000 or less, inhibits the rate of proliferation of endothelial cells. It is only partially purified and characterized and, therefore, is not useful for the treatment of the above-mentioned disorders.

Intraocular neovascularization occurring in diabetic retinopathy is unique in that a therapy exists whereby regression of new blood vessels can be induced and future neovascularization inhibited. This therapy is based on the observation that diabetic intraocular neovascularization rarely occurs in eyes with chorioretinal scars. This has led to the widespread use of argon laser and xenon photocoagulation to therapeutically induce chorioretinal scar formation. The production of photocoagulation induced chorioretinal scars results in a rapid regression of intraocular neovascularization in eyes with proliferative diabetic retinopathy. Such regression occurs even when photocoagulation and resultant chorioretinal scarring occurs in areas remote from the new blood vessels.

Numerous theories have been proposed to explain this phenomenon, but none have as yet been substantiated. One theory suggests that photocoagulation increases the amount of oxygen released into the eye, which is thought to inhibit neovascularization. However, this sequence of events is unproven. Stefansson, et al., *Ophthalmic Surgery*, 14, 209 (1983). Another theory is that photocoagulation destroys retina that releases a stimulus for neovascularization, but this also is unproven. The main reason for doubting the theory is the fact that photocoagulation does not uniformly destroy the inner aspects of the retina where the stimulator for neovascularization is thought to be produced. A third theory is that the photocoagulation allows an escape route for the stimulators of neovascularization to leave the eye. Foulds, *Trans. Ophthalmol. Soc. NZ*, 32, 82 (1980). There is no proof to support this theory either.

The inventor has discovered that cellular components of chorioretinal scars release a substance that inhibits neovascularization and, more specifically, that such inhibitor is released by particular types of cells found in the scars. Chorioretinal scars are composed mainly of astrocytes, retinal pigment epithelial cells, and possibly fibroblasts. Upon testing the ability of these three types of cells to release a substance that causes the regression of new blood vessels in vitro, the present inventor has found that certain retinal pigment epithelial cells and fibroblast cells in culture release such a substance. The substance has been isolated, purified, and characterized.

This discovery is quite unexpected in view of the different theories purporting to explain the effects of chorioretinal scarring and the fact that some recent articles would steer a person skilled in the art away from looking at retinal pigment epithelial cells as a source of neovascularization inhibitor. For example, Korte et al. and Heriot et al. have suggested that retinal pigment epithelial cells may release a substance necessary for blood vessel maintenance. Korte et al., *Invest. Ophthalmol. Vis. Sci.*, 25, 1135 (1984). Heriot et al., *Opthalmology*, 91, 1603 (1984).

The neovascularization inhibitors of the present invention are produced by cultured cells, including retinal pigment epithelial cells of humans and certain other animals and human fibroblast cells. This provides major advantages over the method of producing neovascularization inhibitors from cartilage, vitreous, and lens by extraction. First, the yield of inhibitor is significantly greater than for the extraction process because very large quantities of inhibitor can be produced by using techniques well-known in the art for mass cell culture. The production of sufficient quantities of neovascularization inhibitor permits its isolation, purification, and characterization for further study and also permits sufficient production for commercial applications, such as the treatment of the previously mentioned disorders. Second, the ability to culture cells that produce the inhibitor provides the opportunity to isolate the DNA coding for the active substance, introduce the DNA into bacteria or other organisms, and achieve large-scale synthesis of the active molecule. The employment of such genetic engineering techniques should allow the production of neovascularization inhibitors more cheaply than with mass cell culture techniques and would allow the modification of the molecule to produce analogs with possibly enhanced activity.

SUMMARY OF THE INVENTION

This invention relates to neovascularization inhibitors, processes for their production, and processes for their use in the treatment of disorders in humans or animals in which neovascularization plays a role, including diabetic retinopathy, senile macular degeneration, tumor growth, rheumatoid arthritis, and excessive scarring during wound healing.

An object of the present invention is to provide purified and substantially purified neovascularization inhibitors and biologically active analogs. The inhibitors are recovered from culturable cells, particularly human cells, such as fibroblasts and retinal pigment epithelial cells. They are also recovered from the retinal pigment epithelial cells of animal eyes that lack a tapetum, such as pig eyes. The inhibitors are stable in an acid environment, including an environment where the pH is approximately from 2 to 3. The biologically active analogs are polypeptides with at least one active site having neovascularization inhibitor activity, which site may exhibit substantial homology to the natural neovascularization inhibitor recovered from human retinal pigment epithelial cells or may function in a manner biologically equivalent to such inhibitor recovered from such cells. The site may also be altered to form a polypeptide having enhanced neovascularization inhibitor activity. In accordance with a preferred embodiment of the present invention, the neovascularization inhibitor is a polypeptide with a molecular weight of approximately $57,000 \pm 3,000$ and an isoelectric point of approximately $4.6 \pm 0.3$, which is recovered from human retinal pigment epithelial cells.

In accordance with the present invention, there is provided a process for producing a neovascularization inhibitor by culturing retinal pigment epithelial cells or human fibroblast cells to produce a culture medium containing the inhibitor and recovering the neovascularization inhibitor from the culture medium. There is also provided a process for producing a neovascularization inhibitor by gathering retinal pigment epithelial cells or human fibroblast cells and extracting the inhibitor from the cells. It is preferred that the retinal pigment epithelial cells are obtained from animal eyes that lack a tapetum, most preferably human or pig eyes. It is also preferred that the human fibroblast cells are skin fibroblast cells.

The inhibitor may be purified or substantially purified on the basis of its physical and chemical characteristics, particularly its hydrophobicity and molecular weight. In a preferred embodiment, the inhibitor is produced by growing human retinal pigment epithelial cells in a serum-containing culture medium to superconfluence, removing the medium from the cells, adding serum free medium to the cells and continuing to grow the cells, separating the medium from the cells, subjecting the separated medium to acid dialysis to produce a dialysate, substantially purifying the inhibitor in the dialysate by hydrophobic interaction chromatography, and purifying the substantially purified inhibitor by size exclusion chromatography.

There is also provided a process for producing a neovascularization inhibitor by culturing cells that produce such an inhibitor and are capable of growing in a culture medium to produce a culture medium containing the neovascularization inhibitor, separating the medium from the cells, bringing the medium into contact with immobilized antibodies to a neovascularization inhibitor so as to bind the neovascularization inhibitor to the immobilized antibodies, removing the medium minus the bound inhibitor, and separating the neovascularization inhibitor from the immobilized antibodies. In a preferred embodiment, the separation is accomplished by lowering the pH of the environment of the inhibitor-antibody complex to approximately from 2 to 3 and eluting the inhibitor from the immobilized antibodies.

Also in accordance with the present invention, a process is provided for treating disorders in humans and other animals in which neovascularization plays a role by administering an effective amount of a purified neovascularization inhibitor in admixture with a carrier. The method of administration may be intravenous, topical, intraocular, subconjunctival, intramuscular, or intrathecal administration or by direct injection. The disorders that may be treated include diabetic retinopathy, senile macular degeneration, rheumatoid arthritis, solid tumors, and excessive scarring during wound healing. In a preferred embodiment, a therapeutically effective amount of the neovascularization inhibitor in admixture with a pharmaceutically acceptable carrier is administered intravenously.

This invention also relates to compositions of a therapeutically effective amount of neovascularization inhibitor in admixture with a pharmaceutically acceptable carrier.

Additional objects and advantages of the invention will be set forth in part in the description that follows and in part will be obvious from the description or may be learned from practice of the invention. The objects and advantages may be realized and obtained by means of the instrumentalities and combinations particularly pointed out in the appended claims.

DETAILED DESCRIPTION OF THE INVENTION

Reference will now be made in detail to the presently preferred embodiments of the invention, which, together with the following examples, serve to explain the principles of the invention.

The present invention relates to neovascularization inhibitors, particularly those that have been isolated and produced in a purified or substantially purified form. As used herein, the term "neovascularization inhibitor" means a substance that inhibits the formation of new blood vessels and/or causes the regression of newly formed blood vessels. Preferably, the neovascularization inhibitors of the present invention are polypeptides with a molecular weight of approximately 57,000±3,000, an isoelectric point of approximately 4.6±0.3, and are stable in an acid environment. Such acid environment can have a pH as low as approximately 2–3.

The neovascularization inhibitors of the present invention have been discovered in secretions of retinal pigment epithelial cells and human fibroblast cells and, for the first time, have been isolated and produced in a purified form. For purposes of the present application, "pure" or "purified", when used to refer to the neovascularization inhibitors disclosed herein, shall mean substantially free from other polypeptides that are not neovascularization inhibitor polypeptides. The purified neovascularization inhibitors of the present invention are at least 90% pure and preferably 95% pure.

In addition, it has been discovered that substantially purified neovascularization inhibitors of the present invention have significant anti-neovascularization activity. For purposes of the present application, the term "substantially purified," when used to refer to the neovascularization inhibitors disclosed herein, shall mean inhibitors at least approximately 70% pure.

The neovascularization inhibitors of the present invention may be produced in pure form by the following method:

(a) collecting retinal pigment epithelial cells or human fibroblast cells;

(b) growing the cells in a culture medium;

(c) recovering the neovascularization inhibitor from the medium; and (d) purifying the neovascularization inhibitor.

In a preferred form of the present invention, retinal pigment epithelial cells are obtained from human eyes. However, such cells may also be obtained from other animal sources, particularly animal eyes that lack a tapetum. Such eyes are morphologically more similar to human eyes and, therefore, their retinal pigment epithelial cells could be expected to produce higher levels of neovascularization inhibitor than such cells derived from animal eyes having a tapetum. The pig is one such animal whose retinal pigment epithelial cells have been found by the inventor to produce neovascularization inhibitor.

In an alternative embodiment, human fibroblast cells may be used as a source of neovascularization inhibitor. In particular, human skin fibroblast cells are preferred.

The cells may be collected by various means well-known in the art. For example, retinal pigment epithelial cells can be harvested from postmortem human eyes obtained from an eye bank as described by P. A. Campochiaro, J. A. Jerdan, and B. M. Glaser, *Arch. Ophthalmol.*, 102, 1830 (1984), which is incorporated herein by reference. Human fibroblast cells may be obtained from cell lines on deposit at culture depositories. One such cell line is ATCC No. CRL 1554, available from the American Type Culture Collection, 12301 Parklawn Dr., Rockville, Maryland, U.S.A. 20852.

The neovascularization inhibitor producing cells may be grown in culture using methods well-known in the art. In a preferred embodiment, retinal pigment epithelial cells are grown in flasks containing minimal essential medium with serum (for example Eagle's minimum essential medium with 20% fetal bovine serum (MEM/20)). However, any culture medium designed for the growth of mammalian cells will be appropriate. The cells are placed into the medium at a density of approximately $6.6 \times 10^5$ cells per 75 cm$^2$ flask. Superconfluence is reached at approximately 10 to 11 days after the cells are initially placed into the medium. Dexamethasone, preferably in a concentration of approximately $10^{-7}$ M, may be added to the medium after the cells reach superconfluence in order to enhance the production of inhibitor. After the cells reach superconfluence, the flasks are rinsed to remove the fetal bovine serum, and essential medium without serum is added. The removal of the serum aids in the recovery and purification of the inhibitor, but it is not essential to the practice of this invention. After a period of from approximately 24 to 72 hours and preferably 48 hours, the conditioned medium, i.e., the medium containing the neovascularization inhibitor, is removed and centrifuged to separate the remaining cells, which are removed. In an alternative embodiment, the retinal pigment epithelial cells may be grown to subconfluence which occurs approximately 3 to 4 days after the cells are initially placed into the medium at the above density. After the cells reach subconfluence, Dexamethasone, preferably in a concentration of $10^7$ M, may be added The medium may be washed to remove fetal bovine serum, and serum free medium may be added. The cells are then permitted to grow in the serum free medium prior to the removal of the medium for recovery of the inhibitor. Human fibroblast cells, particularly skin fibroblast cells, may be substituted for retinal pigment epithelial cells in the above process and alternative embodiment.

The neovascularization inhibitor is isolated from the medium and purified by techniques well-known in the art. Such techniques include electrophoresis, centrifugation, gel filtration, precipitation, dialysis, chromatography (including ion exchange chromatography, affinity chromatography, immunoadsorbent affinity chromatography, reverse-phase high performance liquid chromatography, and gel permeation high performance liquid chromatography), isoelectric focusing, and variations and combinations thereof. One or more of these techniques are employed sequentially in a procedure designed to separate molecules according to their physical and chemical characteristics. These characteristics include the hydrophobicity and the molecular weight of the inhibitor. The various fractions of materials obtained after each technique are tested for their ability to inhibit neovascularization or cellular processes involved in neovascularization. Three of these tests are described in Examples 3, 4, and 5 below. Those fractions showing anti-neovascularization activity are then subjected to the next technique in the sequential procedure, and the new fractions are tested again. The process is repeated until only one fraction having the ability to inhibit neovascularization remains and that fraction produces only a single band when subjected to polyacrylamide gel electrophoresis.

In a preferred embodiment, the conditioned medium from which the cells have been removed is dialyzed in an acidic environment through cellulose membranes designed to remove all material of a molecular weight less than 3,500. The pH of such environment is preferably from approximately 2 to 3. Such dialysis in an acidic environment appears to remove substances that interfere with the activity of the neovascularization inhibitor; however, it is not essential to the practice of this invention. It should also be noted that such dialysis can be performed at any stage of the purification process, although it is preferred that it be performed immediately after recovery and centrifugation of the conditioned medium. The dialysate, which contains the neovascularization inhibitor, may be centrifuged in order to remove any suspended solids that could interfere with subsequent purification techniques. However, such centrifugation is not essential to the practice of this invention. The resulting supernatant is subjected to hydrophobic interaction chromatography, in particular reverse-phase high performance liquid chromatography which results in a neovascularization inhibitor that is approximately 70% pure. At this point, the substance has significant anti-neovascularization activity. Final purification is achieved by size exclusion chromatography, in particular gel permeation high performance liquid chromatography, which results in a neovascularization inhibitor that is approximately 95% pure.

In an alternative embodiment of the invention, neovascularization inhibitors may be extracted directly from retinal pigment epithelial cells or human fibroblast cells by techniques well-known in the art. One such technique involves extraction by guanidine hydrochloride using the method disclosed in Williams, et al., *Am. J. Ophthalmol.*, 97, 366 (1984), which is hereby incorporated by reference. Following extraction, the neovascularization inhibitor may be purified by other techniques well-known in the art, including those discussed above.

The discovery and purification of neovascularization inhibitor from human retinal pigment epithelial cells has allowed the production of antibodies to the inhibitor. Antibodies are highly specific and have high affinities for the polypeptides they have been raised against. When attached to an insoluable matrix, they allow the easy and efficient separation of the polypeptide they have been raised against from a complex mixture of proteinaceous and other substances. The methods of using such antibodies are well-known in the art and are disclosed in R. Scopes, *Protein Purification Principles and Practice* (New York: Springer Verlag 1982), pgs. 132–136, which is incorporated herein by reference. Thus, it is now possible for the first time to recover purified neovascularization inhibitor from any cell that produces it by using antibodies to the neovascularization inhibitor derived from human retinal pigment epithelial cells and techniques well-known in the art. Therefore, such purified neovascularization inhibitors are within the scope of this invention.

In a preferred embodiment, purified neovascularization inhibitors are recovered from any type of cell that produces such an inhibitor and is capable of being cultured. The method comprises:

(a) culturing cells that produce a neovascularization inhibitor and are capable of growing in a culture medium;

(b) separating the inhibitor-containing medium from the cells;

(c) bringing the medium into contact with immobilized antibodies to an inhibitor so as to bind the inhibitor in the medium to the antibodies;

(d) removing the medium minus the bound inhibitor; and (e) separating the inhibitor from the immobilized antibodies so as to recover it in a purified form.

Cells may be evaluated for their ability to produce a neovascularization inhibitor by many techniques known in the art, including those disclosed in the instant specification. Those types of cells that are capable of being grown in a culture medium can be cultured by well-known techniques, including those disclosed in the instant specification. However, antibodies may also be used to recover neovascularization inhibitor from cells that are not capable of growing in culture through known extraction or recovery techniques, although it is likely that only a limited amount of purified inhibitor will be recovered.

Antibodies to neovascularization inhibitors may be made by various techniques well-known in the art. Polyclonal antibodies may be made by injecting an inhibitor into rabbits, goats, horses, or other animals. The animals are then bled, and the presence of antibodies can be determined by such methods as double diffusion or detection of antibody-antigen aggregates using $^{125}$I-labeled protein A. The antibodies to inhibitor are then recovered from the serum. Generally, it is necessary only to partially purify the antibodies. In an alternative embodiment, monoclonal antibodies may be used instead of polyclonal antibodies.

The antibodies need not be made by using as the antigen the particular inhibitor sought to be recovered or produced. Since neovascularization inhibitors produced by different types of cells are expected to be identical or substantially homologous to each other, an antibody to an inhibitor such as that recovered from human retinal pigment epithelial cells would be expected to bind to a neovascularization inhibitor produced by a different type of cell.

Various techniques may be used to immobilize the antibodies and then to bring them into contact with the supernatant that contains the neovascularization inhibitor. The technique of immunoadsorbent affinity chromatography is preferred In this technique, the antibodies are coupled to an adsorbant, such as cyanogen-bromide-activated agarose, in a column. The supernatant is run through the column at a rate slow enough so that inhibitor can fully interact with the immobilized antibodies. The column may be washed and then eluted to remove the inhibitor from the antibodies. Detergents or other buffers could be used to separate the inhibitor, but it is preferable to remove the inhibitor from the column by lowering the pH to approximately 2 to 3 and eluting the inhibitor.

It is possible to conceive of a class of neovascularization inhibitors having common elements of structure and mechanism of action and differing from one another in only a few amino acid residues. In addition to being isolated from cells, members of such class could be produced by chemical modifications of existing members by techniques well-known in the art once such members were identified by the teachings of the present invention. Such modifications may enhance the activity of the original inhibitor or may have no effect on such activity. In addition, the present invention allows the cloning of the gene coding for the active inhibitor. Once this gene is cloned, numerous modifications of the active material can be made via base substitution and introduction of the modified gene into a variety of hosts. Thus, it is contemplated that such a class of neovascularization inhibitors is within the scope of the present invention.

It is also contemplated that the neovascularization inhibitors of the present invention may contain one or more amino acid sequences that are not necessary to their activity. Such sequences can be removed by techniques well-known in the art. Unnecessary amino acid sequences could be readily removed via limited proteolytic digestion using enzymes such as trypsin or papain or related proteolytic enzymes. Thus, such inhibitors are within the scope of the present invention.

The neovascularization inhibitors of the present invention can be used to treat disorders in which neovascularization plays a role. For example, they can be used to inhibit neovascularization in diabetic retinopathy and senile macular degeneration. In addition, they can be used to inhibit the formation of blood vessels supplying invading tumors and thereby play a role in inducing tumor regression. They can be used to prevent the invasion of articular cartilage in rheumatoid joints by neovascular tissue. In addition, they can be used to inhibit neovascularization where excessive scarring of the skin, gut, or other bodily organs causes problems. The inhibitors can also be used to control other disorders in which neovascularization during wound healing causes problems, such as occurs in corneal neovascularization following a number of corneal insults by trauma, infections, and degenerations.

The neovascularization inhibitors of the present invention are contemplated for human and veterinary uses in the form of pharmaceutical products posessing neovascularization inhibitor activity. Such pharmaceutical preparations contain, as at least one of the active ingredients, the present neovascularization inhibitor and also appropriate, pharmaceutically acceptable carriers, diluents, fillers, binders, and other excipients depending on the dosage form contemplated. For oral administration, steps must be taken to prevent degradation of the active protein in the digestive track. Enteric coated dosage forms are contemplated as one form suitable for oral administration. It is also contemplated that pharmaceutical preparations containing a neovascularization inhibitor can be administered locally, as by injection or topical application, intravenously, intraocularly, subconjunctivally, intramuscularly, and intrathecally. The mode of administration will necessarily depend upon the disease involved.

The amount of the neovascularization inhibitor to be administered would depend upon the particular disorder being treated. Such a determination is routinely made by those of ordinary skill in the art in determining therapeutic dosages and is within the scope of tasks routinely performed by them without undue experimentation. However, on the basis of in vitro experiments involving the effect of the neovascularization inhibitor of the present invention upon fetal bovine aortic endothelial cell survival, it is believed that a large excess of the neovascularization inhibitor of the present invention would not be toxic or cause an adverse reaction when administered to a human or other animal.

It is to be understood that application of the teachings of the present invention to a specific problem or environment will be within the capabilities of one having ordinary skill in the art in light of the teachings contained herein. Examples of the products of the present invention, process for its production, and process for its use appear in the following examples.

EXAMPLE 1

Preparation of Retinal Pigment Epithelial Cell Culture

Retinal pigment epithelial (RPE) cells were harvested from postmortem human eyes obtained from the Medical Eye Bank of Maryland as described in P. A. Campochiaro, J. A. Jerdan, and B. M. Glaser, *Arch. Ophthalmol.* 102, 1830 (1984). The cells were grown in 75 cm$^2$ flasks containing Eagle's minimal essential medium with 20% fetal bovine serum (MEM/20) in 5% $CO_2$ at 37° C. RPE cells were subcultured once a week. Second to fourth passage cells were used.

EXAMPLE 2

Preparation of RPE Cell Conditioned Medium

Retinal pigment epithelial cell conditioned medium (RPE-CM) was prepared as follows. RPE cells were plated in 75 cm$^2$ tissue culture flasks at a density of $6.6 \times 10^5$ cells in 20 ml of MEM/20. The medium was changed every 3 days. After 6 days, the culture had reached confluence. At confluence, RPE cells reached a density of 3.5 to $4.0 \times 10^6$ cells per 75 cm$^2$ flask. Each flask was then rinsed 3 times with 10 ml Hank's balanced salt solution. Following the last rinse, 10 ml of Eagle's minimal essential medium without serum (MEM/0) were added to each flask. Forty-eight hours later, the conditioned medium was removed and centrifuged to remove RPE cells. The supernatant (RPE-CM) was stored at −20° C. for later use. RPE cells were also grown in Eagle's minimal essential medium with 10% fetal bovine serum (MEM/10) prior to transfer to MEM/0 with identical results. RPE-CM derived from confluent cultures was used in the experiments described in Examples 3–7 below.

Alternatively, to determine the effect of cell density, the medium was conditioned 3 to 4 days after plating the cells for experiments using subconfluent cultures and 10 to 11 days after plating for experiments using superconfluent cultures. The RPE-CM derived from subconfluent and superconfluent cultures was used in the experiments described in Examples 5 and 8 below.

EXAMPLE 3

RPE-CM Inhibition of New Blood Vessels on Chick Embryonic Yolk Sac

The effect of RPE-CM on the vasculature of the chick embryonic yolk sac was evaluated using a modification of the technique described by Taylor and Folkman S. Taylor and J. Folkman, *Nature* 297, 307 (1982). Three day old fertilized White Leghorn chicken eggs were opened and their contents carefully placed in a hammock of plastic wrap suspended in a small plastic drinking cup so that the chick embryo and vascularized yolk sac were fully exposed. The eggs were incubated at 37° C. for 6 hours. The conditioned medium was concentrated 5-fold by ultrafiltration using an Amicon YM10 filter. Filter discs (13 mm diameter; HATF 01300; Millipore, MA) had a 4 mm circle punched out of their central portion and were soaked for 1 hour in the concentrated conditioned medium. The filter discs were then placed on the vascularized yolk sacs. Twenty-four hours later, the yolk sac vasculature within the central cutout of the filter disc was observed for signs of regression using a Zeiss operating microscope (Mag=260 x). The effects of conditioned media on the yolk sac vasculature within the central cutout of the filter disc were graded as to whether there was (+) or was not (−) regression of blood vessels. Regression was considered present if at least 75% of the area within the central cutout of the filter had become avascular.

Discs of filter paper soaked in medium conditioned by RPE cells (RPE-CM), when placed on the surface of the vascularized yolk sac, caused regression of adjacent capillaries resulting in a localized avascular zone. Histologic examination of yolk sac vessels adjacent to RPE-CM soaked filters showed vessels occluded by platelets and packed red blood cells. This is similar to the appearance of regressing vessels in the cornea.

EXAMPLE 4

Effect of RPE-CM on Fetal Bovine Aortic Endothelial (FBAE) Cell Proliferation Rifkin et al. have reported that plasminogen activator and collagenase production are increased when bovine capillary endothelial cells are stimulated by retinal extract. D. B. Rifkin J. L. Gross, D. Moscatelli, and E. Jaffe [in *Pathobiology of the Endothelial Cell*, H. L. Nossel and J. H. Vogel Eds. (Academic Press, New York, 1982), pp. 191–197]. Glaser et al. have reported that FBAE cells also respond to retinal extract (RE) with an increase in the release of plasminogen activator and collagenase. B. M. Glaser, T. Kalebic, S. Garbisa, T. B. Connor Jr., and L. A. Liotta [in *Development of the Vascular System*, Ciba Foundation Symposium 100, J. Nugent and M. O'Connor, Eds. (Pitman, London, 1983), pp. 158–162]. T. Kalebic, S. Garbisa B M. Glaser, L. A. Liotta, *Science* 221, 281 (1983). Therefore, in regard to these biologic markers, FBAE resemble capillary endothelial cells. Furthermore, neovascularization inhibitors from cartilage, aorta, and lens have been shown to inhibit the proliferation of endothelial cells from large blood vessels as well as capillaries. R. Eisenstein, N. Sorgente, L. S. Soble, A. Miller, K. E. Kuettner, *Am. J. Pathol.* 73, 765 (1973); S. B. Goren, R. Eisenstein, E. Chromokos, *Am. J. Ophthalmol.* 84, 305 (1977); G. A. Williams, R. Eisenstein, B. Schumacher, K. Hsiao, D. Grant, *Am. J. Ophthalmol.* 97, 366 (1984). Given these considerations, endothelial cells from both large and small blood vessels are sensitive to inhibitors of neovascularization.

Fetal bovine aortic endothelial (FBAE) cells were grown in 75 cm$^2$ Falcon flasks containing MEM/10 using the techniques described in Glaser et al., *J. Cell Biol.* 84, 298 (1980). The cells were incubated at 37° C. and 5% $CO_2$ and subcultured twice a week. Cultures between passage 4 and 13 were used for all experiments. All experiments were repeated with endothelial cells from 3 different preparations with identical results.

The cultured FBAE cells were plated in 24-well plates (Falcon) at a density of 45,000 cells per well in MEM/10 and incubated at 37° C. in 5% $CO_2$. After 16 hours, the wells were rinsed with MEM/0 and filled with 1 ml of either MEM/0 or RPE-CM with or without added retinal extract (RE) diluted 1:20. RE was obtained as described in B. M. Glaser, P A. D'Amore, R. G Michels, A. Patz, A. Fenselau, *J. Cell Biol.* 84, 298 (1980). Twenty-four hours later the cells were trypsinized and counted with a Coulter counter. The concentration of all undiluted conditioned media ranged between 400 and 500 ug/ml as determined by the method of Lowry et al., using bovine serum albumin as a standard. O. H. Lowry, N. J. Rosebrough, A. L. Farr, R. J. Randall *J. Biol. Chem.* 193, 265 (1951).

The effect of preincubating FBAE cells with various concentrations of RPE-CM prior to the addition of RE was also determined. Sixteen hours after the cells were plated they were rinsed with MEM/0. Various dilutions of conditioned media in MEM/0 were then added to the wells of one plate. In a duplicate plate all wells were filled with MEM/0 alone. The final volume in each well was 1 ml. Twenty-four hours later, RE was added to each well to achieve a final dilution of 1:20. After an additional 24 hours, the cells were trypsinized and counted.

RPE-CM inhibited the proliferative response of FBAE cells to retinal extract. The ability of RPE-CM to inhibit FBAE cell proliferation in response to retinal extract was enhanced by pretreating the FBAE with RPE-CM for 24 hours prior to adding the retinal extract.

In order to determine if RPE-CM could inhibit FBAE proliferation in response to other stimuli, the effect of RPE-CM on fetal bovine serum induced FBAE cell proliferation was studied. The growth of FBAE cells after 24 hours in 5% fetal bovine serum was reduced by 60% in the presence of RPE-CM.

EXAMPLE 5

Effect of RPE-CM on Proteases Involved in Neovascularization

One of the first steps in neovascularization is the localized dissolution of the extracellular matrix at the future site of a new vessel sprout. The activation of plasminogen by plasminogen activators to generate the protease plasmin seems to play an important role in this process. Therefore, it is believed that neovascularization inhibitors would inhibit plasmin or plasminogen activators.

Human RPE-CM was found to inhibit plasmin mediated degradation of $^{125}$I-labeled fibrin and plasmin mediated degradation of the synthetic substrate H-D-Val-L-Leu-L-Lys-p-nitroaniline. Furthermore, the RPE-CM inhibited the rate at which urokinase-like plasminogen activators degraded the synthetic substrate N-Cbz-Arg-AMC. In addition, the release of retinal pigment epithelial cell derived protease inhibitor was abolished by inhibitors of RNA (actinomycin-D) and protein (cycloheximide) synthesis. In contrast, inhibition of cell division (hydroxyurea) did not reduce inhibitor release. Subconfluent and superconfluent cultures of human RPE cells provided significantly more inhibitory activity than confluent cultures.

EXAMPLE 6

Reversibility of the Inhibitory Effect of RPE-CM

FBAE cells were grown in MEM/0, MEM/0 plus RE, or RPE-CM plus RE as described in Example 4. After 24 hours, the FBAE cells were tryspinized and counted. At the same time, identical cultures grown in MEM/0 or MEM/0 plus RE were rinsed and refilled with fresh media identical to what they had been growing in, whereas wells containing RPE-CM plus RE were rinsed and refilled with fresh MEM/0 plus RE. After an additional 24 hours the cells were trypsinized and counted. Removal of RPE-CM restored the rate of FBAE cell proliferation to that of control cultures growing without RPE-CM. Therefore, the inhibitory effect of RPE-CM was reversible.

EXAMPLE 7

Effect of RPE-CM on FBAE Cell Survival

To determine if RPE-CM is toxic to vascular endothelial cells FBAE cells were grown in concentrated RPE-CM for 24 hours. RPE-CM, at concentrations used on the chick vasculature, showed no toxicity for FBAE cells as determined by trypan blue exclusion. The ability of RPE-CM to cause regression of vessels was lost after boiling for 10 min. and trypsin treatment.

In addition, the loss of $^{14}C$-thymidine from prelabeled FBAE cell monolayers was used to estimate cell death after the addition of RPE-CM using the method of R. H. Eckel and W. Y. Fujimoto, *Anal. Biochem.* 114, 118 (1981). FBAE cells were cultured as described in Example 4. Cells were plated into 75 cm$^2$ flasks at a concentration of $2 \times 10^6$ cells/flask and incubated with MEM/10 containing 0.004 uCi $^{14}C$-thymidine/ml for 4 days. The prelabeled cells were then trypsinized and plated in 24 well plates at a concentration of 45,000 cells/well as described above. After 16 hours, the wells were rinsed with MEM/0 and filled with MEM/0 or various concentrations of RPE-CM diluted with MEM/0. All wells received RE diluted 1:20. The plates were reincubated at 37° C. and 5% CO$_2$ for an additional 24 hours. At this time, 1 uCi of $^3H$-thymidine was added to each well, and the plates were reincubated for 2 hours. $^{14}C$-thymidine or $^3H$-thymidine content of cells was determined as described in B. M. Glaser, P. A. D'Amore, R. G. Michels, A. Patz, and A. Fenselau, *J. Cell Biol.* 84, 298 (1980). The addition of RPE-CM to FBAE cells did not result in the loss $^{14}C$ thymidine but did inhibit cell proliferation as indicated by a decrease in $^3H$-thymidine uptake.

The series of experiments described in Examples 4–7 suggests that RPE-CM does not act as a cell toxin but acts as a relatively specific inhibitor of vascular endothelial cell proliferation.

EXAMPLE 8

Effect of RPE Cell Density on Release of Inhibitor

In all experiments described so far, RPE-CM was harvested from confluent cultures. Therefore, the effect of RPE cell density on the release of neovascularization inhibitor was examined using the FBAE cell proliferation assay described in Example 4. It was discovered that confluent RPE cells produce significantly less inhibitor than subconfluent RPE cells. When the RPE cells were allowed to remain in culture for 4 to 5 days after they reached confluence (superconfluent cultures), the inhibitory activity of the conditioned medium increased once again. Corresponding to this increase in inhibitory activity, the RPE cells began to overgrow the monolayer and form localized regions with multiple cell layers. Therefore, as RPE cells formed a confluent monolayer, the inhibitory activity of the conditioned medium was reduced. When the cultures later became overgrown and the RPE cells escaped the confines of the monolayer, they again increased their production of inhibitor.

EXAMPLE 9

Neovascularization Inhibitor from RPE Cells from Pig Eyes

Serum-free medium condition by pig RPE cells (27 ug protein/ml) was prepared in accordance with the techniques described in Examples 1 and 2. Such medium was tested according to the method of Example 3 and found to inhibit neovascularization.

EXAMPLE 10

Purification of RPE Cell-Derived Inhibitor of Neovascularization

Preparation of RPE-CM

RPE-CM was prepared by plating RPE cells in 75 cm$^2$ tissue culture flasks at a density of $6.6 \times 10^5$ cells in 20 ml of MEM/20. The medium was changed every 3 days. After 10 to 11 days RPE cell cultures had become superconfluent. At this point the medium in each flask was changed to MEM/20 supplemented with $10^{-7}$ M dexamethasone. After an additional 24 hours, each flask was then rinsed 3 times with 10 ml Hank's balanced salt solution. Following the last rinse, 10 ml of MEM/0 supplemented with $10^{-7}$ M dexamethasone were added to each flask. Forty-eight hours later, the conditioned medium was removed and centrifuged. The supernatant was stored at $-20°$ C. for later use.

Preparation of RPE-CM for Chromatography

The supernatant was dialyzed (MW cutoff=3,500) for 16 hours against 0.1% trifluoroacetic acid (TFA) in water. The dialysate was then centrifuged at 20,000 rpm for 20 min. at 4° C.

Reverse-Phase High Performance Liquid Chromatography

Column: uBondapak C18, $19 \times 150$ mm, Waters Inc
Solvents: A: 0.1% TFA in water; B: 0.1% TFA in isopropanol
Flow Rate: 11.25 ml/min
Detector: Waters 441 at 214 nm.

The column is initially equilibrated with solvent A. Twenty to thirty ml of RPE-CM, prepared as above, were injected onto the column at the indicated flow rate. After the absorbance of the column effluent returned to baseline, the column was eluted with a linearly increasing gradient of solvent B until the concentration of B reached 35%. Flow was continued with this solvent mix for 8 min. The concentration of solvent was then stepped up to 38% and held at this level for 8 min. Next, the concentration of solvent B was then stepped up to 40%, and the column was eluted with this solvent mix for an additional 5 min. Material eluting from the column during elution with a 40% B solvent mix was collected. This fraction contained the RpE cell inhibitor of neovascularization and was approximately 70% pure, as determined by gel permeation chromatography. This fraction was lyophilized.

Gel Permeation High Performance Liquid Chromatography

Column: Bio Rad Preparative Bio-sil TSK 250 21.5×600 mm

Solvent: 0.1% TFA in water and 0.1% TFA in acetonitrile in a 50/50 mixture.

Flow Rate: 3 ml/min.

Detector: Waters 441 at 214 nm.

Lyophilized material from the previous step was dissolved in 1 ml of the above solvent and injected onto the column. A large peak containing active inhibitor eluted with a retention time of approximately 36.5 min. This peak was collected and lyophilized Purity and Characterization The purity of the above material was determined by SDS-polyacrylamide gel electrophoresis. Silver stained gels revealed only a single band with a molecular weight of approximately 57,000±3,000. Isoelectric focusing revealed a pI of approximately 4.6±0.3.

EXAMPLE 11

Neovascularization Inhibitor from Human Fibroblasts

Human skin fibroblasts (ATCC No. CRL 1554) were obtained frozen at passage No. 5 from the American Type Culture Collection. Cells were thawed and plated in a 75 cm$^2$ flask containing 20 ml of Eagle's Minimal Essential Medium with non-essential amino acids and 10% fetal bovine serum. These cells were grown to confluence over seven days. The cells were then split at a ratio of 1:5 and plated in 75 cm$^2$ tissue culture flasks with 20 ml of Eagle's Minimal Essential Medium with 10% fetal bovine serum. After eight days in culture, the medium was removed and the cells were washed three times with Hank's balanced salt solution. The cells were then cultured in 10 ml of Eagle's Minimal Essential Medium without serum for 48 hours. The medium was removed and found to inhibit neovascularization using the same criteria as stated for RPE cell conditioned medium.

The human fibroblast conditioned medium prepared as noted above was subjected to SDS-polyacrylamide gel electorphoresis. A 57,000±3,000 molecular weight species was identified after staining the gel with silver stain. This band migrated to the exact same location as the purified inhibitor from human retinal pigment epithelial cells.

EXAMPLE 12

Purification of Neovascularization Inhibitor by Immunoadsorbent Affinity Chromatography Antibodies to purified neovascularization inhibitor were raised in rabbits using conventional techniques. The rabbits were initially injected with 300 μg of inhibitor in complete Freund's adjuvant. Additonal bimonthly injections of 100-300 in complete Freund's adjuvant were made. The rabbits were bled, and the presence of the antibody was determined by double diffusion. The antibody was then partially purified from the rabbit serum by precipitation at 33% saturation of ammonium sulfate.

The rabbit antibodies may be used in the technique of immunoadsorbent affinity chromatography for purification of the inhibitors described herein. The antibody is coupled to an adsorbent such as cyanogen-bromide-activated agarose. Crude samples containing the inhibitor are then run over the column at a slow rate so that inhibitor can interact fully with the immobilized antibody. The column is washed with loading buffer. Subsequently, the column is eluted to remove the inhibitor from its antibody. Since the inhibitor is stable at a pH of 2-3, it is preferable to remove the inhibitor from the column by lowering the pH to this level, but other techniques using detergents or other buffers could also be used. The purity of the inhibitor is tested by SDS-polyacrylamide gel electrophoresis.

It will be apparent to those skilled in the art that various modifications and variations can be made to processes and products of the present invention. Thus, it is intended that the present invention cover the modifications and variations of this invention provided they come within the scope of the appended claims and their equivalents.

What is claimed is:

1. A process for producing a neovascularization inhibitor comprising the steps of:
   culturing retinal pigment epithelial cells to produce a culture medium containing said neovascularization inhibitor; and
   purifying said neovascularization inhibitor from said medium wherein said neovascularization inhibitor has a molecular weight of approximately 57,000±3,000 and an isoelectric point of approximately 4.6±0.3 and is stable in an environment with a pH of approximately from 2 to 3.

2. A process as recited in claim 1 wherein said retinal pigment epithelial cells are obtained from animals eyes that lack a tapetum.

3. A process as recited in claim 2 wherein said animal eyes are human eyes.

4. A process as recited in claim 2 wherein said animal eyes are pig eyes.

5. A process for producing a neovascularization inhibitor comprising the steps of:
   culturing retinal pigment epithelial cells to produce a culture medium containing said neovascularization inhibitor;
   separating said medium from said cells; and
   substantially purifying said inhibitor by subjecting said medium to hydrophobic interaction chromatography wherein said neovascularization inhibitor has a molecular weight of approximately 57,000±3,000 and an isoelectric point of approximately 4.6±0.3 and is stable in an environment with a pH of approximately from 2 to 3.

6. A process as recited in claim 5 comprising the additional step of purifying said substantially purified inhibitor by subjecting said substantially purified inhibitor to size exclusion chromatography.

7. A process as recited in claim 6 wherein said dialysis is employed at any stage after said medium is separated from said cells.

8. A process as recited in claim 7 wherein said acid dialysis is employed after said medium is separated from said cells and before said step of substantially purifying said inhibitor by hydrophobic interaction chromatography.

9. A process for obtaining a neovascularization inhibitor produced by retinal pigment epithelial cells comprising the steps of:

culturing retinal pigment epithelial cells to produce a culture medium containing a neovascularization inhibitor wherein said neovascularization inhibitor has a molecular weight of approximately 57,000±3,000 and an isoelectric point of approximately 4.6±0.3 and is stable in an environment with a pH of approximately from 2 to 3;

separating said medium from said cells;

bringing said medium into contact with immobilized antibodies to said neovascularization inhibitor so as to bind said neovascularization inhibitor in said medium to said immobilized antibodies; and separating said neovascularization inhibitor from said immobilized antibodies.

10. A process for producing a neovascularization inhibitor comprising the steps of:

growing human retinal pigment epithelial cells in a culture medium;

separating said medium from said cells;

subjecting said separated medium to acid dialysis to produce a dialysate containing said inhibitor;

substantially purifying said inhibitor in said dialysate by reverse-phase high performance liquid chromatography; and purifying said substantially purified inhibitor by gel permeation high performance liquid chromatography wherein said neovascularization inhibitor has a molecular weight of approximately 57,000±3,000 and an isoelectric point of approximately 4.6±0.3 ad is stable in an environment with a pH of approximately from 2 to 3.

11. The process of claim 9 wherein said step of separating comprises lowering the pH of the environment of the inhibitor-antibody complex to approximately from 2 to 3 and eluting said inhibitor from said immobilized antibodies.

12. The process of claim 9 wherein said antibodies are polyclonal antibodies.

13. The process of claim 9 wherein said antibodies are monoclonal antibodies.

* * * * *